United States Patent

Falco et al.

[11] Patent Number: 6,006,361
[45] Date of Patent: *Dec. 28, 1999

[54] HEARING PROTECTION DEVICE

[75] Inventors: Robert N. Falco, Indianapolis; Marc Doty, Brownsburg, both of Ind.

[73] Assignee: Cabot Safety Intemediate Corporation, Southbridge, Mass.

[*] Notice: This patent is subject to a terminal disclaimer.

[21] Appl. No.: 09/065,881

[22] Filed: Apr. 24, 1998

Related U.S. Application Data

[63] Continuation of application No. 08/698,367, Aug. 15, 1996, Pat. No. 5,809,574.

[51] Int. Cl.$^6$ .................................................. A61F 11/14
[52] U.S. Cl. ............................. 2/209; 2/171; 2/DIG. 11; 128/866
[58] Field of Search ....................... 2/171, 209, DIG. 11; 128/864, 866, 867

[56] References Cited

U.S. PATENT DOCUMENTS

| | | | |
|---|---|---|---|
| Re. 29,487 | 12/1977 | Gardner, Jr. . | |
| D. 272,946 | 3/1984 | Scanlon | D24/106 |
| 1,066,511 | 7/1913 | Markoff | 128/866 |
| 2,420,245 | 5/1947 | Hurst | 2/209 |
| 4,193,396 | 3/1980 | Wacker . | |
| 4,253,452 | 3/1981 | Powers et al. . | |
| 4,404,434 | 9/1983 | Pelt et al. | 2/209 |
| 4,461,290 | 7/1984 | Gardner, Jr. et al. . | |
| 4,671,265 | 6/1987 | Andersson . | |
| 4,867,149 | 9/1989 | Falco . | |
| 5,044,463 | 9/1991 | Carr | 128/864 |
| 5,113,967 | 5/1992 | Killion et al. . | |
| 5,188,123 | 2/1993 | Gardner, Jr. . | |
| 5,203,352 | 4/1993 | Gardner, Jr. . | |
| 5,682,608 | 11/1997 | Landis | 2/171 |
| 5,692,243 | 12/1997 | Chang | 2/171 |
| 5,809,574 | 9/1998 | Falco et al. | 2/209 |

*Primary Examiner*—Diana Oleksa
*Attorney, Agent, or Firm*—Cantor Colburn LLP

[57] ABSTRACT

A hearing protection device. The hearing protection device includes a band and legs that are rotatable relative to the band. Each leg includes a first leg end and a second leg end. The first leg end is rotatably coupled to the band to allow the leg to rotate relative to the band. The second leg end includes a hole for receiving a stem of a hearing protector. Alternatively, the second leg end includes a socket for receiving a ball formed on a hearing protector shaft. The hearing protection device can accommodate head sizes ranging from the 5th percentile of women to the 95th percentile of men.

13 Claims, 10 Drawing Sheets

HEARING PROTECTION DEVICE

CROSS-REFERENCE TO RELATED APPLICATIONS

This application is a continuation of U.S. patent application Ser. No. 08/698,367 filed Aug. 15, 1996 now U.S. Pat. No. 5,809,574.

BACKGROUND OF THE INVENTION

1. Field of the Invention

The invention relates generally to hearing protection devices and in particular to a hearing protection device including rotatable legs for adjusting the position of hearing protectors.

2. Prior Art

Hearing protectors fall generally into three categories, including protectors that cap the entrance to the ear canal; protectors which enter the ear canal and seal the ear canal prior to the bend in the ear canal (usually referred to simply as semi-insert devices); and protectors that enter the ear canal and take the bend in the ear canal (sometimes referred to as banded earplugs). Semi-insert hearing protectors generally protect similarly to earplugs, but usually to a lesser level. Semi-insert hearing protectors are also referred to as semi-aural hearing protectors. Semi-insert hearing protectors which enter the ear canal to a greater degree offer better protection but are somewhat less comfortable than those which simply cap the ear. Products which cap the ear have some of the attributes of both earplugs and earmuffs. Typically, they are used for intermittent noise exposures where lighter weight and improved low frequency attenuation are desirable. As used herein, "hearing protectors" refers generally to hearing protectors falling into one of the three categories described above.

FIG. 14 is a front view of a conventional hearing protection device disclosed in U.S. Pat. No. 4,461,290. The hearing protection device includes a U-shaped headband 1 having affixed to each of the opposed end portions 3 and 5 an inwardly directed ear obturating pod 2. A pair of balls 7 and 9 engage a socket formed in the pods 2 and attach the pods 2 to the headband 1. While well-suited for its intended purposes, the conventional headband 1 may have certain drawbacks and deficiencies. For example, the shape of the headband is such that when the pods 2 are mounted in the wearer's ears, portions of the headband 1 are close to or touching the wearer's head. This can be irritating and uncomfortable to the wearer. In addition, there is no mechanism for adjusting the headband to allow for varying head sizes. A wearer with a large head requires a large distance between the headband ends 3 and 5. Unfortunately, as the distance between the headband ends 3 and 5 increases, so does the tension in the headband 1. Accordingly, wearers with large heads may experience discomfort due to this high tension in the headband 1. In order to accommodate varying head sizes, the headband 1 must be manufactured in multiple sizes which increases manufacturing costs. Accordingly, there is a perceived need in the art for a hearing protection device that can comfortably fit a wide variety of head sizes.

SUMMARY OF THE INVENTION

The above-discussed and other drawbacks and deficiencies of the prior art are overcome or alleviated by the hearing protection device of the invention. The hearing protection device includes a frame having a band and a pair of leg supports. A pair of legs are rotatably coupled to the leg supports. Each leg has a first leg end rotatably coupled to a respective leg support and a second leg end for receiving a hearing protector. Each second end has a mating means (preferably an opening) for receiving a stem portion of the hearing protector. In an alternative embodiment, the frame of the hearing protection device includes a band portion and a pair of reverse curve portions integral with the band portion. The reverse curve portion has an oblique angle formed therein and reverse curve ends for receiving hearing protectors. An important feature of the alternative embodiment that as a result of the reverse curve portions, the hearing protectors at the ends of the band will not come in contact with a surface after having been placed thereon; thereby leading to improved sanitary conditions since the hearing protectors will be less likely to be contaminated.

The hearing protector in accordance with this invention provides several important features and advantages relative to the prior art. For example, the rotatable legs allow the band to accommodate virtually any head size and provide the wearer with both comfort and a variety of wearing positions.

The above-discussed features and advantages of the present invention will be appreciated and understood by those skilled in the art from the following description and drawings.

BRIEF DESCRIPTION OF THE DRAWINGS

Referring now to the drawings wherein like elements are numbered alike in the several FIGURES.

DETAILED DESCRIPTION OF THE INVENTION

Figure 2:
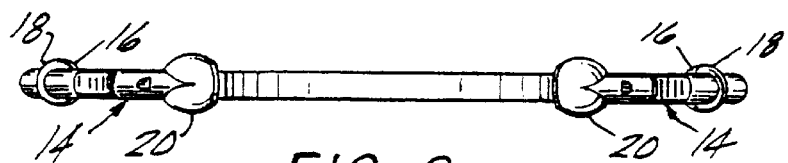
FIG. 2 is a top view of the frame of FIG. 1.
Figure 5:
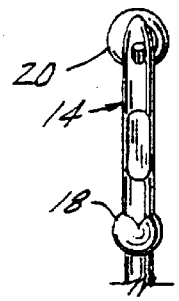
FIG. 5 is a view taken along line 5—5 in FIG. 1.
Figure 1:
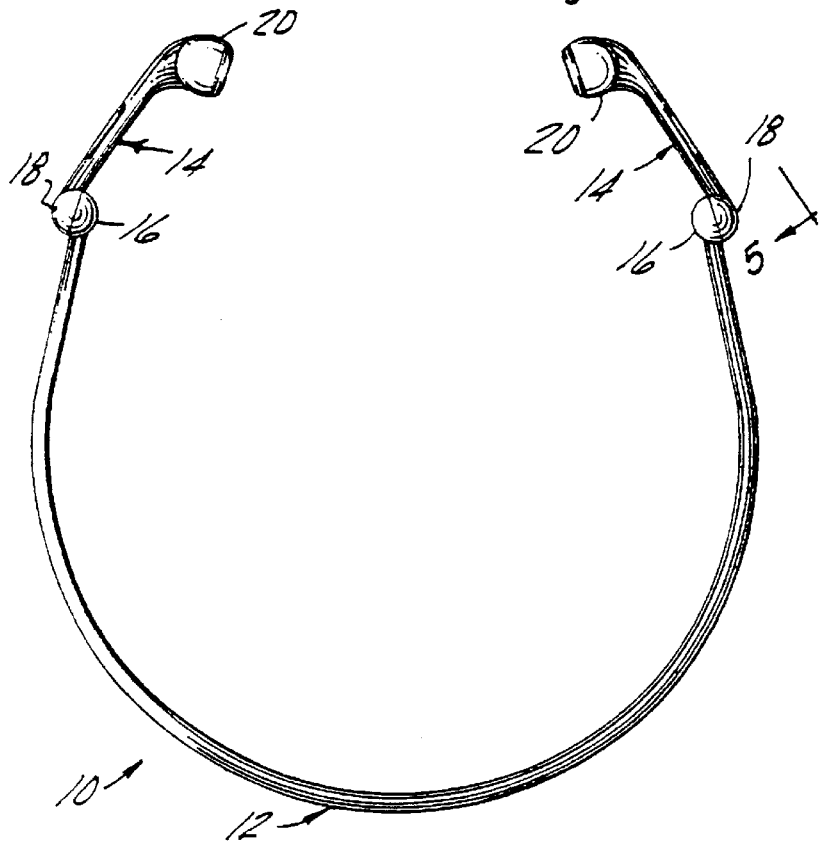
FIG. 1 is a front view of a frame of a hearing protection device in a first embodiment of the invention.
Figure 4:
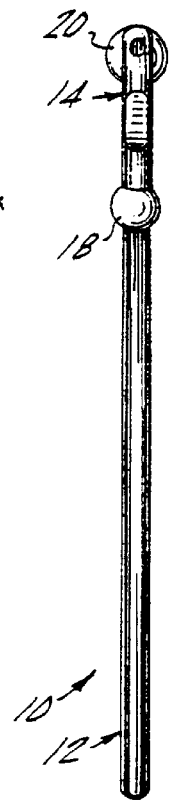
FIG. 4 is a side view of the frame of FIG. 1.
Figure 3:
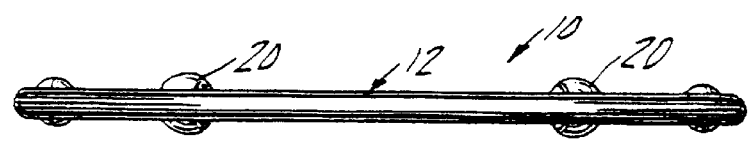
FIG. 3 is a bottom view of the frame of FIG. 1.

FIG. 1 is a front view of the frame of the hearing protection device in a first embodiment of the invention. The frame is shown generally at 10. The frame 10 includes a band 12 and a pair of legs shown generally at 14. The band 12 is generally U-shaped and is made from a resilient, flexible material such as plastic. The band 12 has two leg supports 16, each of which forms one half of a swivel or rotating joint between the band 12 and the leg 14. The leg support 16 is integral with the band 12 and in an exemplary embodiment is a spherical segment. The leg 14 includes a first leg end 18 which is integral with leg 14 and, in an exemplary embodiment, is a spherical segment. The flat faces of the first leg end 18 and the leg support 16 are placed opposite each other to form a swivel joint. The details of the swivel joint are described below with reference to FIGS. 6 and 7. The swivel joint allows the first leg end 18 to rotate relative to the leg support 16 thereby allowing the leg 14 to rotate relative to the band 12. The band 12 lies substantially in a plane and as the legs 14 are rotated, a plurality of angles are defined between the leg 14 and the plane. It is understood that the band 12 and leg supports 16 need not lie in the same plane as shown in FIG. 4. Indeed, as shown in FIGS. 15 A, B and C (and discussed hereafter) the leg supports 16 may lie in a plane different than the band 12 and each leg 14 will rotate through a plurality of angles between the leg 14 and the plane of the leg supports 16. The leg 14 includes a second leg end 20 for receiving a hearing protector 100 (shown in FIGS. 11A and 11B). In an exemplary embodiment, the second leg end 20 is a spherical segment. It will be appreciated that second leg end 20 may comprise any other desired functional shape such as ovular, triangular, etc. The outer dimension of the second leg end 20 is preferably equal to the average concha bowl opening so that the second leg end 20 cannot be inserted into the ear canal but is preferably insertable (and rests in) the concha bowl (so that the earplug attached to end 20 is permitted to freely articulate in the ear canal). FIGS. 2–5 are various views of the frame of the hearing protection device of FIG. 1 and are self-explanatory.

Figure 6:
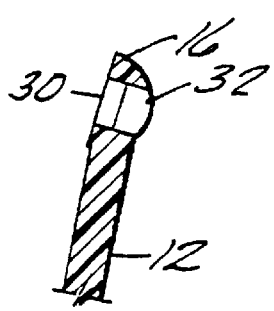
FIG. 6 is a cross-sectional view of one end of a band shown in FIG. 1.
Figure 7:
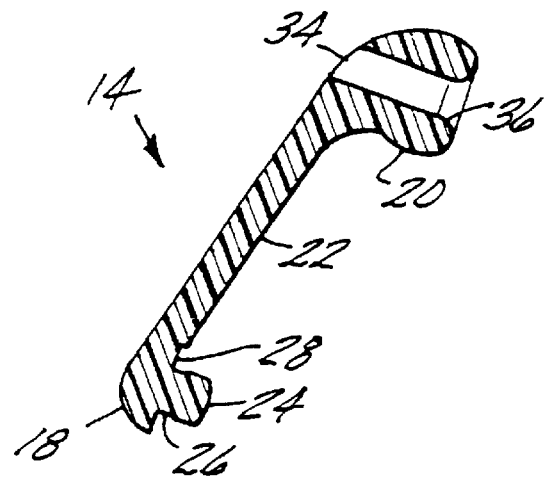
FIG. 7 is a cross-sectional view of a leg shown in FIG. 1.

FIG. 6 is a cross-sectional view of the leg support 16 and FIG. 7 is a cross-sectional view of the leg 14. The leg 14 includes first leg end 18, second leg end 20 and leg body 22. The first leg end 18 has a planar surface 28 and a post 24 substantially perpendicular to the planar surface 28. The post 24 has a neck region 26 where the diameter of the post 24 is smaller than the diameter of the end of the post 24 away from the planar surface 28. The leg support 16 includes a hole 32 formed therethrough for receiving the post 24. The neck 26 snap-lockedly engages a ridge 30 formed in the hole 32. The ridge 30 has an inner diameter that is smaller than the inner diameter of the hole 32. That is, the ridge 30 extends away from the inner wall of the hole 32. The interference fit between the neck 26 and the ridge 30 holds the leg 14 to the band 12 while allowing the post 24 to rotate within the hole 32. Because the band 12 and the leg 14 are made from a resilient material, such as plastic, the interference fit between the neck 26 and the ridge 30 can be defeated by pulling the post 24 out of the hole 32 if necessary.

Figure 8:
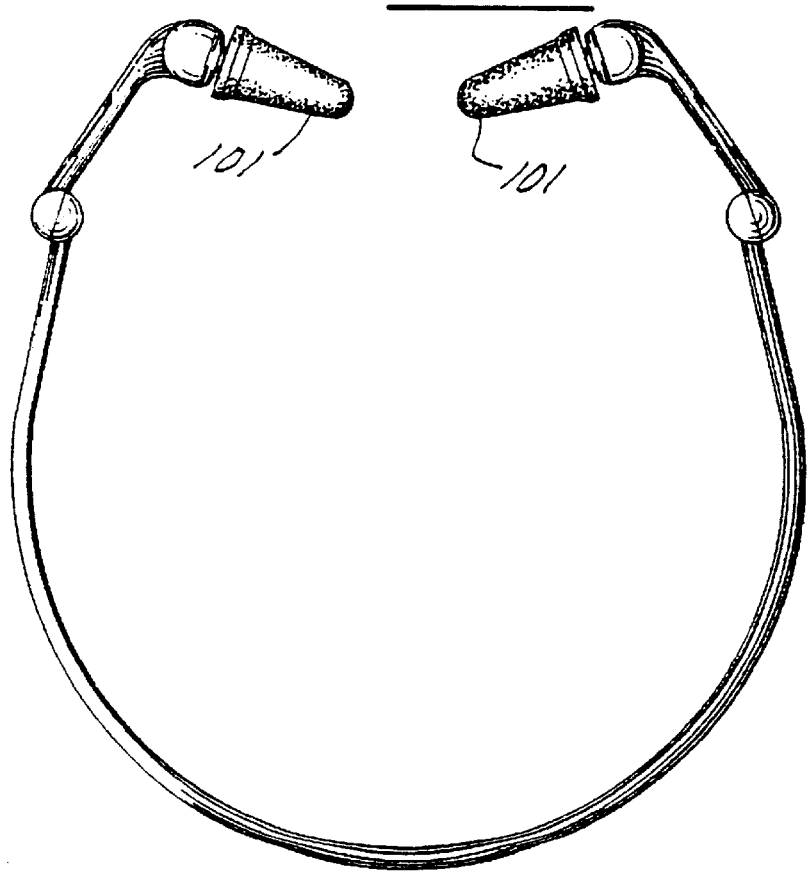
FIG. 8 is a front view of the frame of FIG. 1 fitted with a first type hearing protector.
Figure 9:
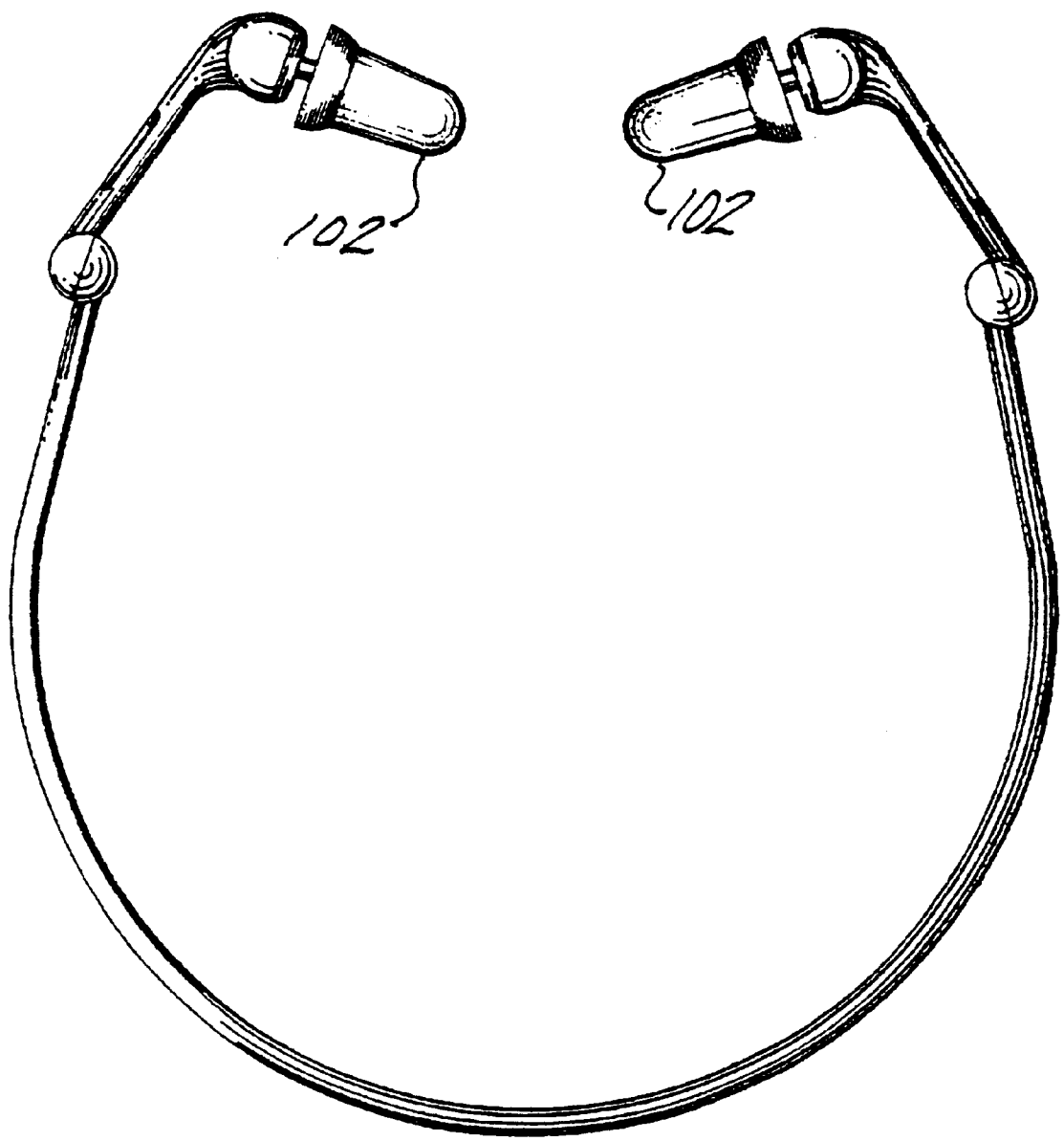
FIG. 9 is a front view of the frame of FIG. 1 fitted with a second type of hearing protector.
Figure 10:
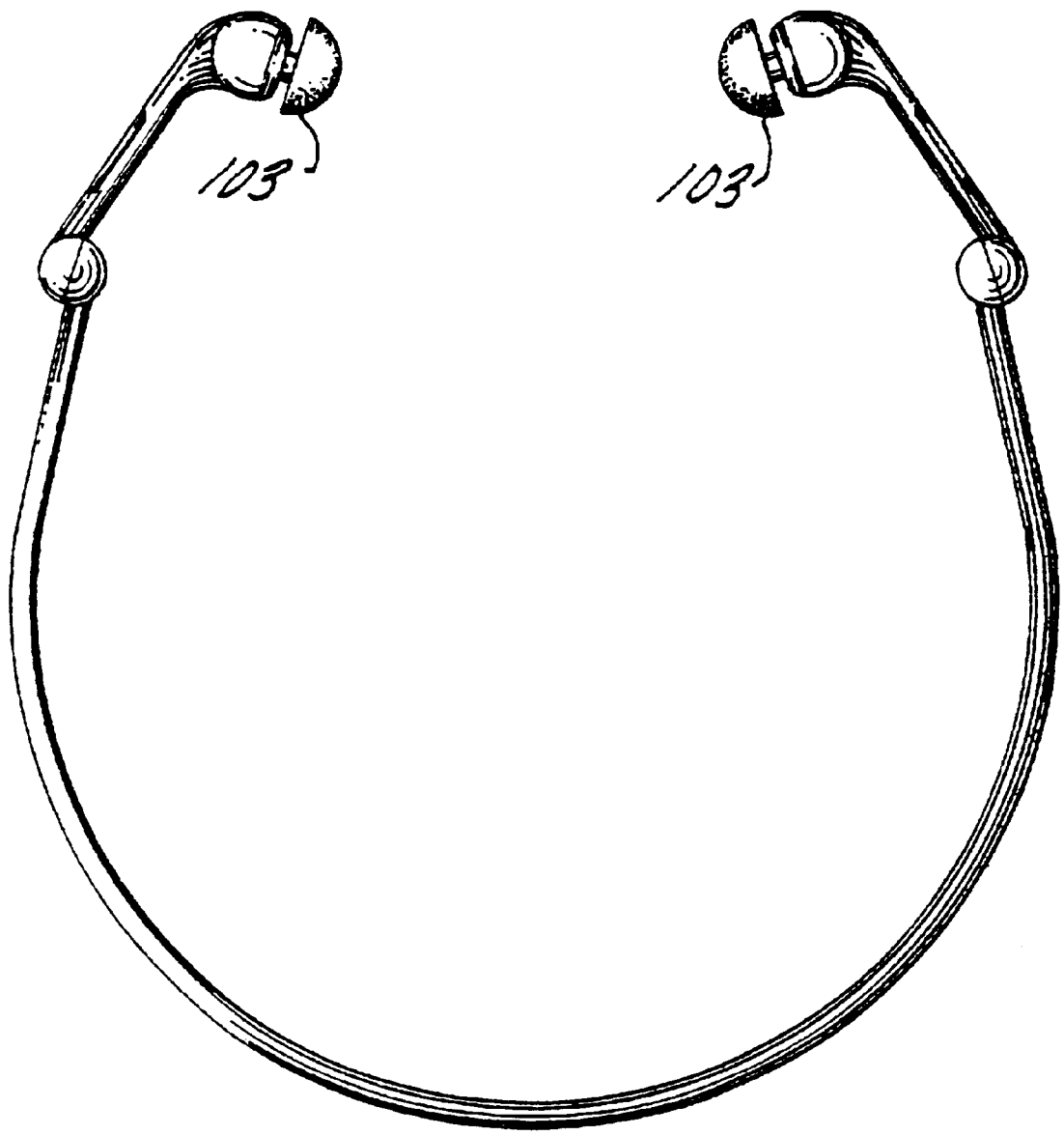
FIG. 10 is a front view of the frame of FIG. 1 fitted with a third type of hearing protector.

The planar surface 28 of the first leg end 18 is at an oblique angle relative to the major axis of the leg body 22. This causes the leg 14 to be angled towards the interior of the U-shaped band 12 as shown in FIG. 1. This results in the second leg ends 20, which hold the hearing protectors as shown in FIGS. 8–10, being close to the wearer's head and the band 12 being away from the wearer's head. Because the band 12 is positioned away from the wearer's head, it is less likely that the band 12 will contact and irritate the wearer. Thus, the comfort of the hearing protection device is improved over the prior art.

Figure 15A:
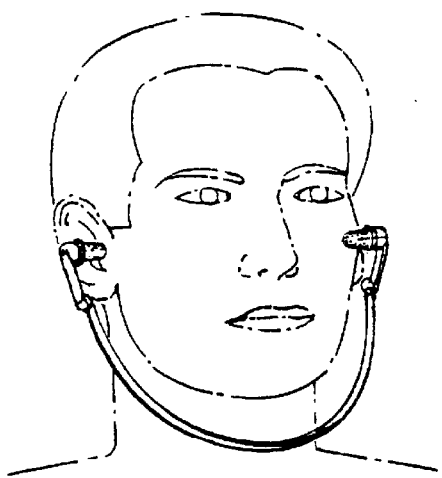
FIGS. 15A–C are perspective views depicting the hearing protective device of this invention in three different positions on a wearer's head.
Figure 15B:
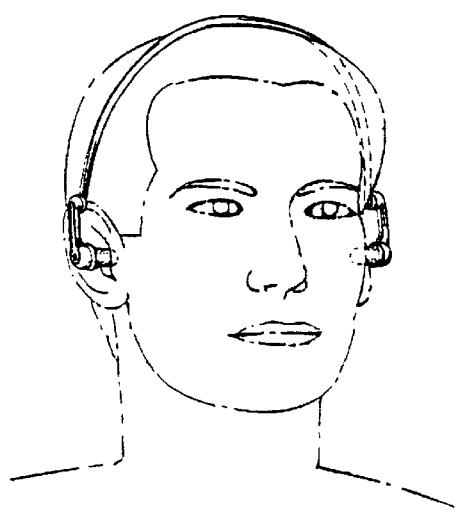
Figure 15C:
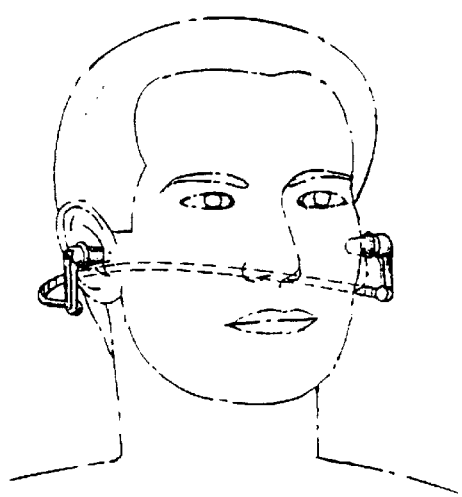

The frame 10 allows the legs 14 to rotate to comfortably accommodate head sizes ranging from, for example, the 5th percentile of women to the 95th percentile of men. The legs 14 may be rotated while the hearing protection device is being worn to allow modification of the fit without removing the hearing protection device. In addition, the hearing protection device can be worn with the band 12 under the chin (as shown in FIG. 15A), over the top of the head (as shown in FIG. 15B), or behind the back of the head based on the wearer's preference (as shown in FIG. 15C).

Figure 17:
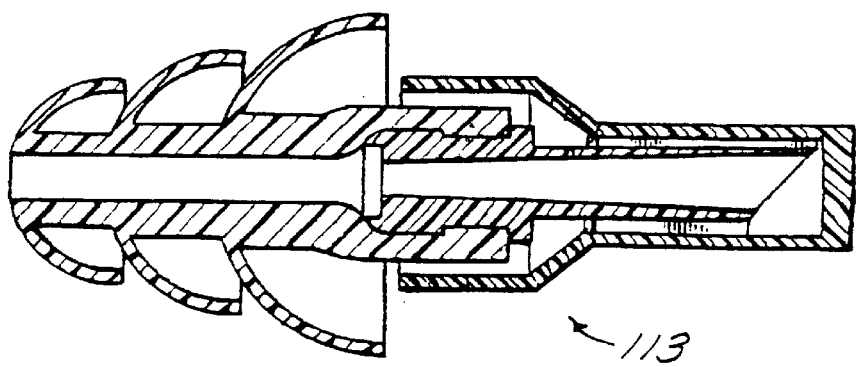
FIG. 17 is a cross-sectional view of a frequency attenuating hearing protector for use with the present invention.
Figure 16A:
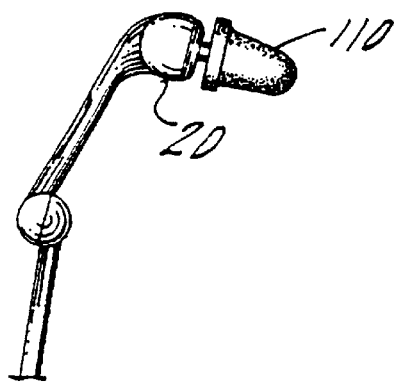
FIGS. 16A–16C are front views of the frame fitted with a variety of hearing protectors.
Figure 16B:
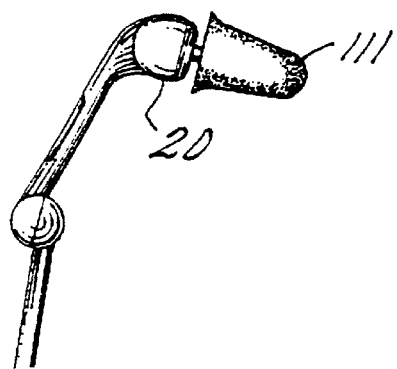
Figure 16C:
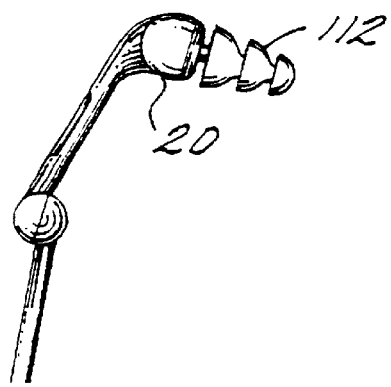

The second leg end 20 includes a hole 34 formed therein for receiving various hearing protectors 101–103 as shown in FIGS. 8–10. As mentioned above, the hearing protectors may be protectors that cap the entrance to the ear canal; protectors which enter the ear canal and seal the ear canal prior to the bend in the ear canal; or protectors that enter the ear canal and take the bend in the ear canal. FIGS. 16A–16C illustrate additional hearing protectors 110–112 that may be mounted to the second leg end 20. FIG. 17 is a cross-sectional view of a hearing protector 113 that may be mounted to the second leg end 20. The hearing protector 113 attenuates sound over a wide frequency range uniformly. Additional details of the hearing protector in FIG. 17 are provided in U.S. Pat. No. 5,113,967, the full contents of which are incorporated herein by reference. The hearing protection device of the present invention provides a comfortable fit regardless of the size or shape of the hearing protectors mounted in the second leg ends 20.

Figure 11A:
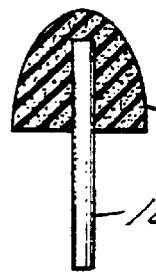
FIGS. 11A–11B are a cross-sectional views of a hearing protectors for use with the hearing protection device of FIG. 1.
Figure 11B:
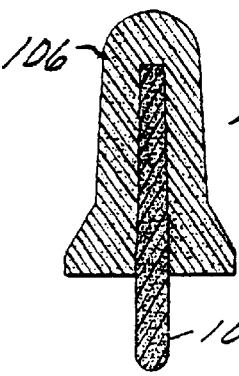

As shown in FIGS. 11A and 11B, a hearing protector 100 comprises a foam portion 106 coupled to a stem 104. The hearing protector in FIG. 11A is a conventional hearing protector in which the foam portion 106 is glued to the stem 104. The hearing protector shown in FIG. 11B is an improved design in which the stem 104 is made from a porous material and the foam 106 interpenetrates the pores in the stem 104 to form a mechanical bond. This hearing protector shown in FIG. 11B is described in additional detail below.

In an exemplary embodiment, the foam portion 106 is a dynamically stiff foam. A suitable dynamically stiff foam is described in commonly assigned U.S. Pat. No. 5,420,381, the contents of which are incorporated herein by reference. Alternatively, the foam portion 106 may comprise any other conventional earplug foam material such as the foam disclosed in U.S. Reissue Pat. No. 29,487, all of the contents of which are also incorporated herein by reference. The stem 104 is placed in the hole 34. The use of hole 34 and stem mounted hearing protector 100 allows the wearer to change hearing protectors easily. Hole 34 includes a curved area 36 (shown in FIG. 7) that eases placement of the hearing protector 100 in hole 34. The stem 104 is preferably flexible so that it flexes as the wearer adjusts the hearing protection device. A non-pliable stem may cause discomfort as the wearer adjusts the hearing protection device. By using a flexible stem 104, an extra degree of freedom is introduced into the hearing protection device. The foam portion 106 moves along with the wearer's head and provides additional comfort.

To provide a tight fit in the hole 34, the stem 104 should be made from a compressible, resilient material and have a diameter slightly larger than the diameter of hole 34. When the stem 104 is positioned in hole 34, the stem 104 will press against the wall of hole 34 and provide a friction fit. The hole 34 need not be formed completely through the second leg end 20 for the stem 104 to be securely mounted to the second leg end 20. However, if the hole 34 is formed all the way through the second leg end 20, the stem 104 can be pushed out of the second leg end 20 to aid removal of the hearing protector 100 if necessary.

As previously mentioned with reference to FIG. 11B, in an exemplary embodiment, the stem 104 is made from a porous material, such as that disclosed in the U.S. patent application filed contemporaneously herewith entitled "Hearing Protective Device Comprising a Foam and a Porous Component, and Method of Manufacturing Thereof" which is incorporated herein by reference. The porous material is both flexible and compressible. The porous material is preferably a polymer or combination of polymers in the form of small particles of one or more size ranges bonded in such a way as to leave voids or pores within the material. The pores may be of varying sizes. Preferably, the pore volume is in the range from about ten percent to about ninety percent of the total volume, with the most preferred pore volume being in the range from about thirty to about sixty percent of the total volume. A particularly preferred porous component is Swab-002 made from INTERFLO®, available from Interflo Technologies, Brooklyn, N.Y. The foam 106 interpenetrates the pores in the porous stem 104 to mechanically bond the foam portion 106 to the stem 104.

Figure 14:
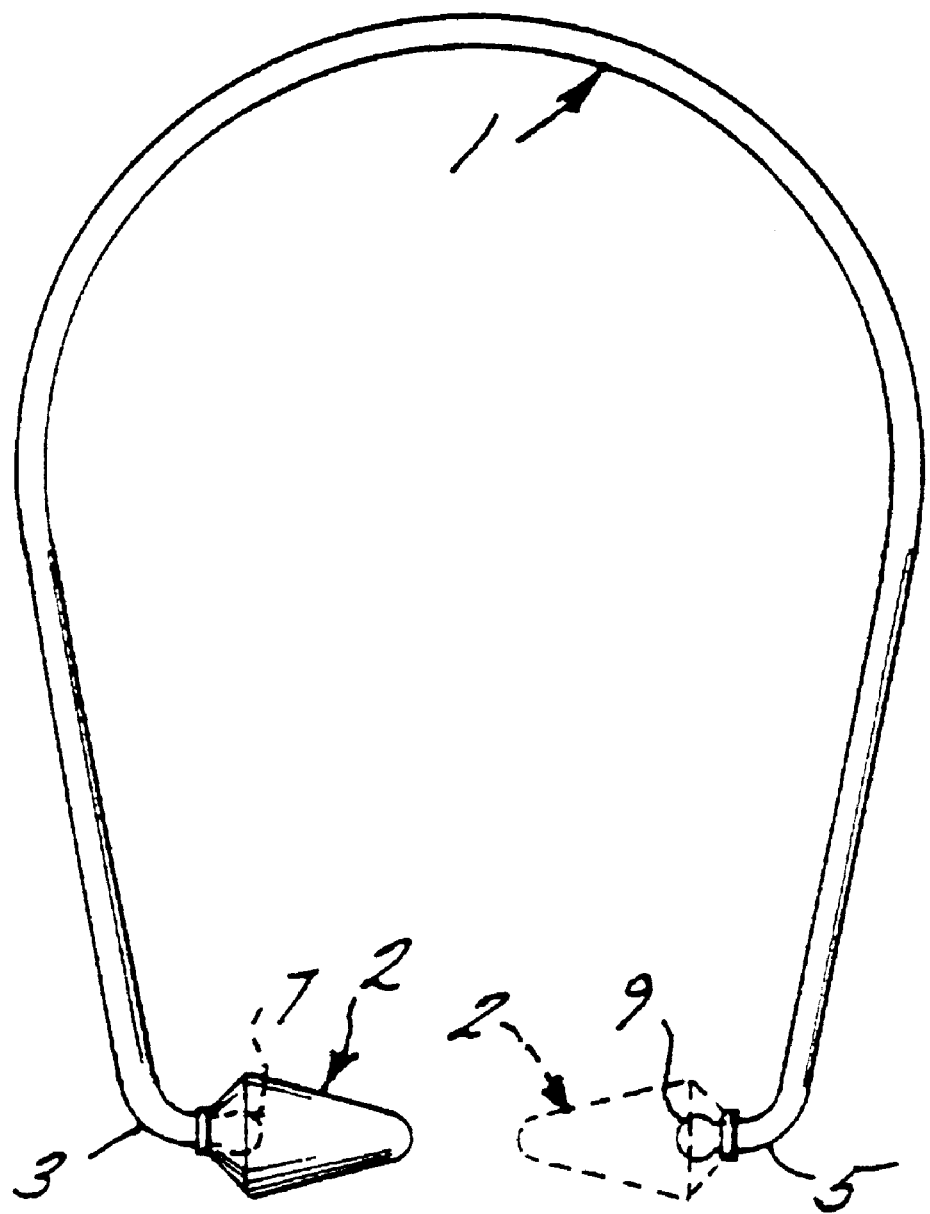
FIG. 14 is a front view of a conventional hearing protection device.

It will be appreciated that an ear protective device may be mounted to the ends of legs 14 in any suitable manner in addition to the hole 34 with mating stem 104 approach shown in the preferred embodiments. For example, a foam or other earplug device could be attached using a ball and socket configuration as in prior art FIG. 14, or any other approach may be used whereby the earplug is attached to leg 14.

Figure 12:
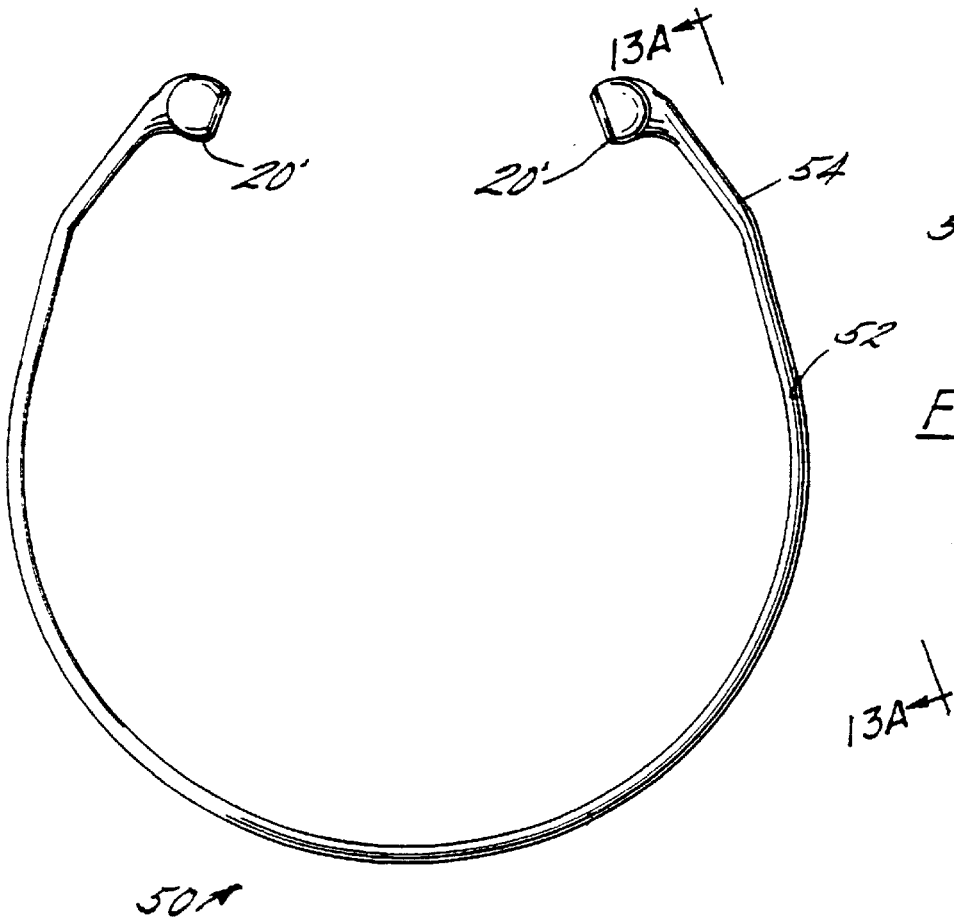
FIG. 12 is a front view of a frame of a hearing protection device in a second embodiment of the invention.

FIG. 12 is a front view of an alternative frame for a hearing protection device. The frame is shown generally at 50 and includes a band portion 52 and reverse curve portions 54. The reverse curve portions are integral with the band portion 52. The center of gravity is located within the band portion 52. The reverse curve portions 52 each includes a reverse curve end 20' which is similar to the leg second ends 20 described above with reference to FIGS. 1–7. The reverse curve portion 54 includes an oblique angle α. The angle α directs the reverse curve ends 20' of the reverse curve portions 54 towards the wearer's head. This provides additional space between the band 52 and the wearer's head which reduces the likelihood that the band 52 will contact or irritate the wearer.

Figure 13A:
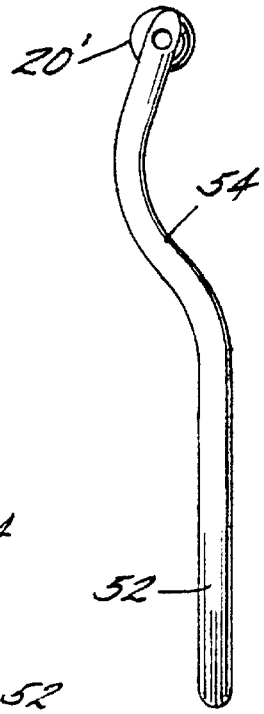
FIG. 13A is a view taken along line 13A—13A of FIG. 12.

FIG. 13A is a view of the frame 50 taken along line 13A—13A of FIG. 12. The reverse curve ends 20' of the reverse curve portions 54 receive the stem 104 of the hearing protector 100 as shown in FIG. 11B. The use of a hearing protector 100 having a flexible stem 104 is also advantageous to the fit of the hearing protection device shown in FIG. 12. As described above, this allows the foam portion 106 of the hearing protector 100 to move relative to the reverse curve end 20', and provides a more comfortable fit.

Figure 13B:
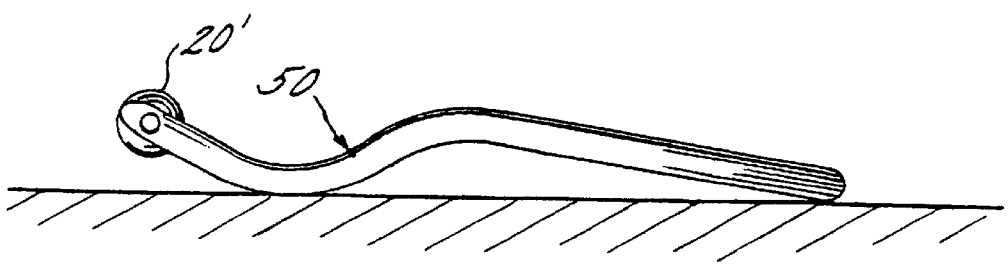
FIGS. 13B–13C are side views of the frame of FIG. 12 placed on a surface.
Figure 13C:
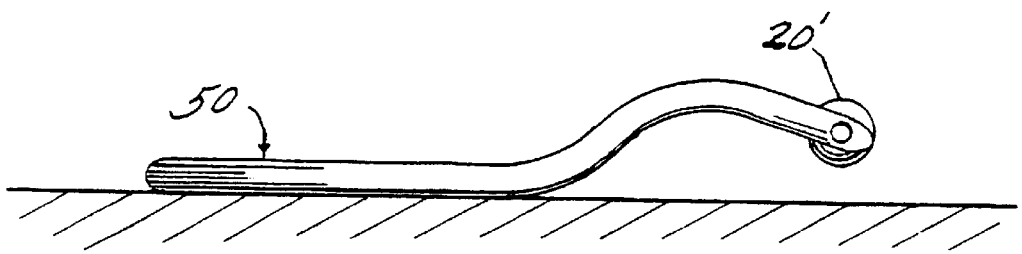

The reverse curve portions 54, along with the location of the center of gravity within the band 52, reduce the likelihood that the hearing protectors mounted in reverse curve ends 20' will become contaminated when the frame 50 is placed on a surface. As shown in FIGS. 13B and 13C, when the frame 50 is placed on a surface in either orientation, the reverse curve ends 20' are positioned above the surface. This reduces the likelihood that the hearing protectors mounted in the reverse curve ends 20' will become contaminated and thereby leads to improved sanitary conditions.

Figure 18:
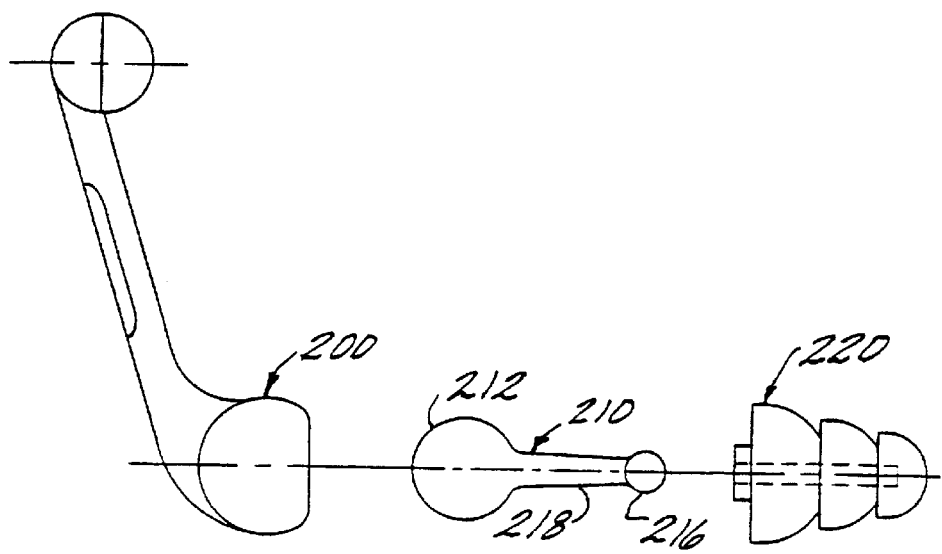
FIG. 18 is an exploded view of an alternative system for mounting a hearing protector to the frame.

FIG. 18 is an exploded view of an alternative system for mounting a hearing protector to the frame. A shaft 210 includes a first ball 212 and a second ball 216 joined by a shaft neck 218. The first ball 212 engages a socket 202 (shown in FIG. 19) formed in the frame end 200. The socket 202 may be formed in either the second leg end 20 shown in FIG. 1 or the reverse curve end 20' shown in FIG. 12. The second ball 216 engages a hearing protector 220. The hearing protector 220 shown in FIG. 18 is a multiple flange earplug similar to the earplug described in U.S. Pat. No. 4,867,149, the full contents of which are incorporated herein by reference. It is understood, however, that any hearing protector may be configured for use with shaft 210.

Figure 19:
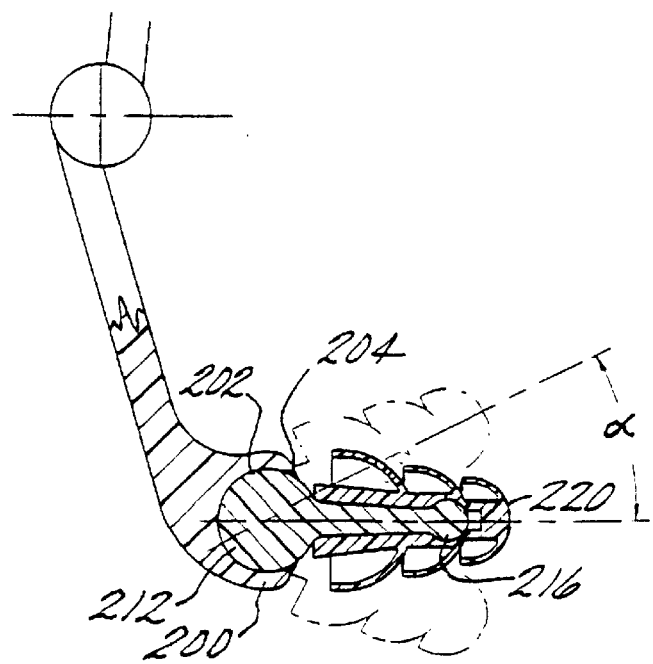
FIG. 19 is a partial cross-sectional view of a hearing protector mounted to the frame using the system of FIG. 18.

FIG. 19 is a partial cross sectional view of the hearing protector 220 mounted to the frame end 200 through shaft 210. The first ball 212 is placed within socket 202. The socket 202 includes a lip 204 that extends into the socket 202 to reduce the diameter of the opening of the socket 202. The outer diameter of the first ball 212 is slightly smaller than the inner diameter of the socket 202. The frame end 200 is made from a resilient material (e.g., plastic) and the lip 204 flexes to allow the first ball 212 to be placed within the socket 202. The lip 204 then returns to its original position once the first ball 212 is placed in the socket 202. The interference fit between the lip 204 and the first ball 212 retains the shaft 210 in the frame end 200. As previously mentioned, either the second leg end 20 or the reverse curve end 20' may include the socket 202 and lip 204. The hearing protector 220 is then placed on the shaft 210 and retained on the shaft by the interference fit between the second ball 216 and the hearing protector 220.

The mounting system of FIGS. 18 and 19 allows the hearing protector 220 to rotate away from a center line of the socket 202 by an angle α. FIG. 19 illustrates the hearing protector 220 in three different positions. In an exemplary embodiment, α equals 27°. The use of the ball and socket mounting system shown in FIGS. 18 and 19 introduces additional degrees of freedom in the hearing protection device. This allows the wearer to finely adjust the position of the hearing protectors for a more comfortable fit.

The present invention provides a hearing protection device that comfortably fits head sizes ranging from the 5th percentile of women to the 95th percentile of men. This is accomplished through legs having a first end rotatably coupled to a band and a second end for receiving hearing protectors. To increase comfort, the hearing protector may be mounted on a flexible stem which allows the hearing protector to move relative to the leg. Alternatively, a ball and socket mounting system may be used to allow the wearer to finely adjust the position of the hearing protectors relative to the frame.

While preferred embodiments have been shown and described, various modifications and substitutions may be made thereto without departing from the spirit and scope of the invention. Accordingly, it is to be understood that the present invention has been described by way of illustration and not limitation.

What is claimed is:

1. A hearing protection device comprising:
   a band having a pair of ends;
   a pair of legs, each of said legs having a first end rotatably coupled to one of said band ends and a second end for receiving a hearing protector, said legs being rotatable with respect to said band while said hearing protection device is worn; and a hearing protector coupled to the second end of each leg.

2. The hearing protection device of claim 1 wherein said band lies substantially in a plane and an angle exists between said each of said legs and said plane, said angle varying as said leg is rotated.

3. The hearing protection device of claim 1 wherein said band ends lie substantially in a plane and an angle exists between said each of said legs and said plane, said angle varying as said leg is rotated.

4. The hearing protection device of claim 1 wherein said legs are rotatable into a plurality of orientations with respect to said band including:

a first orientation wherein the band is positioned beneath a wearer's chin;

a second orientation wherein the band is positioned at the top of the wearer's head; and a third orientation wherein the band is positioned at the back of the wearer's head.

5. The hearing protection device of claim 1 wherein said legs are rotatable into a plurality of orientations with respect to said band including:

a first orientation wherein the band is positioned beneath a wearer's chin.

6. The hearing protection device of claim 1 wherein each of said second ends has an outer dimension substantially equal to an average concha bowl opening.

7. The hearing protection device of claim 1, wherein said hearing protector is a cap.

8. The hearing protection device of claim 1, wherein said hearing protector is a semi-insert device.

9. The hearing protection device of claim 1, wherein said hearing protector is an ear plug.

10. The hearing protection device of claim 1, wherein said hearing protector includes a stem and a foam portion connected to said stem.

11. The hearing protection device of claim 10, wherein said stem is made from a porous material.

12. The hearing protection device of claim 11, wherein said stem includes pores and said foam portion interpenetrates said pores to mechanically bond the foam portion to said stem.

13. A hearing protection device comprising:

a band having a pair of ends;

a pair of legs, each of said legs having a first end coupled to one of said band ends and a second end for receiving a hearing protector, the leg being coupled to the band end to provide movement of the leg relative to the band; and a hearing protector coupled to the second end of each leg, the hearing protector being coupled to the second end of the leg to provide movement of the hearing protector relative to the leg;

wherein said band ends lie substantially in a plane and each of said legs has a body having a major axis, an angle exists between said major axis of each of said legs and said plane, said angle varying as said leg is rotated.

* * * * *

UNITED STATES PATENT AND TRADEMARK OFFICE
CERTIFICATE OF CORRECTION

PATENT NO. : 6,006,361
DATED : December 28, 1999
INVENTOR(S) : Robert N. Falco, et. al.

It is certified that error appears in the above-indentified patent and that said Letters Patent is hereby corrected as shown below:

Column 2, line 47, delete "a" after "are"
Column 2, line 47, delete "a" after "of"
Column 4, line 49, delete " arc" and insert therefor --are--
Column 5, line 44, delete "52" second occurrence and insert therefor --54--

Signed and Sealed this

Thirteenth Day of March, 2001

Attest:

NICHOLAS P. GODICI

Attesting Officer

Acting Director of the United States Patent and Trademark Office